United States Patent [19]

Guadagno

[11] Patent Number: 4,725,553
[45] Date of Patent: Feb. 16, 1988

[54] TEST COMPOSITION FOR DETECTING OCCULT BLOOD

[75] Inventor: Philip A. Guadagno, Vidor, Tex.
[73] Assignee: Helena Laboratories Corporation, Beaumont, Tex.
[21] Appl. No.: 752,758
[22] Filed: Jul. 8, 1985

Related U.S. Application Data

[62] Division of Ser. No. 537,213, Sep. 29, 1983, Pat. No. 4,541,987.

[51] Int. Cl.$^4$ ............... G01N 21/78; G01N 33/72
[52] U.S. Cl. ............... 436/66; 252/408.1; 422/61; 422/56; 436/904
[58] Field of Search ............... 422/61, 56, 58; 436/66, 436/67, 904; 252/408.1

[56] References Cited

U.S. PATENT DOCUMENTS

| | | | |
|---|---|---|---|
| 2,838,377 | 6/1958 | Fonner | 436/66 |
| 3,092,464 | 6/1963 | Adams et al. | 436/66 |
| 3,672,351 | 6/1972 | Ubersax et al. | 422/56 |
| 4,219,336 | 8/1980 | Guthlein et al. | 436/66 |

FOREIGN PATENT DOCUMENTS

| | | |
|---|---|---|
| 0085261 | 8/1983 | European Pat. Off. |
| 7712266 | 11/1979 | Netherlands |
| 1018563 | 1/1966 | United Kingdom |

*Primary Examiner*—Barry S. Richman
*Assistant Examiner*—C. M. Delahunty
*Attorney, Agent, or Firm*—Cullen, Sloman, Cantor, Grauer, Scott & Rutherford

[57] ABSTRACT

A test pad having a water activated reagent and a water activated peroxygen compound which undergo a chromogen reaction in an aqueous solution including hemoglobin. The reagent is potassium guaiacolsulfonate, a guaiac substitute material. The peroxygen compound is a monopersulfonate compound comprised of two moles of potassium monopersulfonate, one mole of potassium hydrogen sulfate and one mole of potassium sulfate. The test pad features a test area containing the above materials in powdered form and may also include controls for checking the results of the test. A method for using the test pad is also disclosed.

3 Claims, 6 Drawing Figures

TEST COMPOSITION FOR DETECTING OCCULT BLOOD

CROSS-REFERENCE TO RELATED APPLICATION

This is a division of application Ser. No. 537,213, filed Sept. 29, 1983, now U.S. Pat. No. 4,541,987.

BACKGROUND OF THE INVENTION

1. Technical Field

This invention relates generally to a method and apparatus for detecting the presence of blood in an aqueous solution. More specifically, the present invention relates to a method and apparatus in which a dry reagent and dry peroxygen compound are packaged in a test pad for in-home testing of fecal material or urine in a toilet bowl.

2. Prior Art

Early detection of gastrointestinal cancers is vital to successful treatment. One sign of gastrointestinal cancer is the presence of blood in fecal material or urine. Frequently when blood is visible the cancer has already progressed to a late stage. Tests for detecting blood in such samples before it is visible are very useful but have suffered from certain problems and deficiencies.

U.S. Pat. No. 2,838,377 to Fonner discloses one method for detecting the presence of occult, unseen, blood in feces and urine. In Fonner, an envelope of sheet material contains a dried reagent material that is adapted to be dropped into a toilet bowl containing water and either feces, urine or both with the reagent changing color if blood is present in the solution. The reagent mixtures are selected from the group consisting of o-tolidine, benzidine, or o-toluidine. The primary disadvantage of the Fonner test is that the reagents used are either suspected or known carcinogens. Another problem with the Fonner test is its lack of specificity causing it to frequently yield a positive test result when no blood is actually present in the sample.

U.S. Pat. No. 3,996,006 to Pagano discloses a specimen test slide comprising of a multi-fold cardboard package having a sheet of test paper impregnated with a guaiac based reagent material enclosed therein. The test is performed by applying samples of feces on one side of the test paper after opening a flap formed in the test slide and sending the test slide to a laboratory for analysis. Laboratory analysis is performed by applying a peroxide solution to the opposite side of the test paper and observing the test paper to determine whether a color reaction caused by the presence of blood occurs. The necessity of handling fecal material and sending the specimen to a laboratory for later analysis is a serious disadvantage of the Pagano test.

U.S. Pat. No. 4,175,923 to Friend discloses a method for determining the presence of occult blood in the bowl of a toilet by first spraying a developing solution of ethyl alcohol and hydrogen peroxide on a sheet of guaiac impregnated test paper and then dropping the test paper into the bowl. One problem with Friend is that patients are reluctant to use liquid reagents. Also, the ethyl alcohol and hydrogen peroxide solution is caustic which may cause irritation if it comes into contact with a patient's skin. Even though the above problems are encountered when an activating solution of hydrogen peroxide is applied to a test pad, Friend teaches that such a solution is essential for a test using a guaiac reagent in a cold water environment.

Various other tests for the presence of occult blood in fecal material and urine samples have been proposed, however, none have realized the advantages of the present invention wherein a patient may conveniently test for the presence of occult blood in a toilet bowl without the use of carcinogenic materials and without the need for activating solutions.

SUMMARY OF THE INVENTION

The present invention relates to a method and apparatus for determining the presence of blood in an aqueous solution containing a sample to be tested wherein a pad having a solid peroxyen compound and a solid guaiac substitute reagent is floated on the surface of the solution and observed for a chromogen reaction. The term "guaiac substitute" refers to a chromogen which may be utilized in place of guaiac.

The breakthrough achieved by the preferred chemistry of the invention is that the reagents are soluable and functional in a cold water environment without using an activating solution and without using known carcinogenic materials.

The guaiac substitute reagent is preferably guaiacolsulfonate and the peroxygen compound is preferably potassium monopersulfate. The guaiac substitute reagent and peroxygen compound are both water soluble and become activated upon contact with the aqueous solution. The chromogen reaction will occur even if only a small amount of blood is present in the sample and is therefore very sensitive. The preferred reagents are not easily catalyzed by oxidants other than hemoglobin or hemin based substances which makes the test very specific.

In accordance with the present invention, the test for occult blood does not require handling of reagent materials or activating solutions. The test is performed entirely within the toilet bowl and does not require sending samples or specimens to a laboratory for further analysis or testing.

Another aspect of the present invention is the provision of controls on a test pad to verify the accuracy of the test. A comparative positive site (positive control) may be included on the test pad that would include the same reagent and peroxygen compound as used in the test pad test area plus a small amount of catalyst material that should always yield the positive test results. If a negative result is indicated on the positive control the test should be repeated with another test pad because the first test pad falsely indicated that the test result was negative when all of the components for a positive test were present in the test pad.

A comparative negative site (negative control) may also be included in the test pad for indicating falsely positive results and for comparison with the test area if the test area indicates that no blood is present. The negative control would include a substance similar in appearance to the contents of the test area such as the dry peroxygen powder without inclusion of the guaiac substitute reagent. Since the guaiac substitute reagent is not present in the negative control, under no circumstances should a chromogen reaction occur. The negative control also permits the test area to be compared to the negative control wherein if no color reaction occurs the two areas should have the same appearance.

The invention will be better understood upon studying the following detailed description with reference to the drawings.

DETAILED DESCRIPTION OF THE INVENTION

Figure 1:
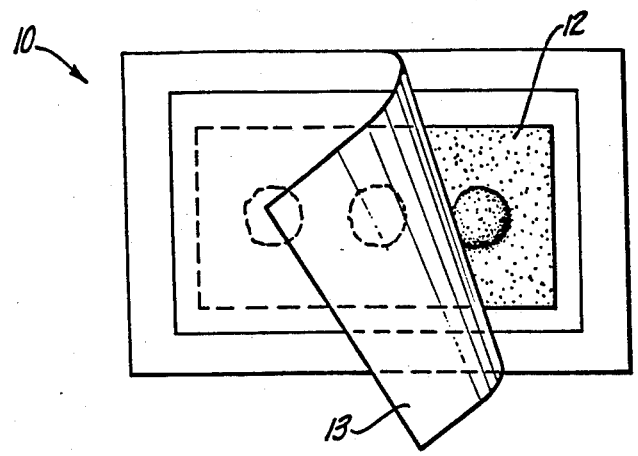
FIG. 1 is a plan view of a test pad disposed in a sealed envelope with the top layer of the sealed envelope partially removed for access to the test pad.

Referring now to FIG. 1, the test kit 10 is shown to include a test pad 12 which is enclosed within the envelope 13. The envelope provides a hermetically sealed pocket for the test pad to protect it from contamination or exposure to moisture during shipment and storage. The test pad 12 includes a top layer of an absorbant material, preferably paper, and a bottom layer 16 likewise formed of a absorbant material such as paper. Between the top and bottom layers 15 and 16, pockets are formed for enclosing a dry powder material.

A test area 17 is provided which includes a reagent material and a dry peroxygen compound. The test area 17 is the area on the test pad 12 which undergoes a chromogen reaction when the test pad 12 is placed in a toilet bowl containing water and fecal material containing blood. If occult blood is present, even in small amounts, the chromogen reaction should occur.

The test area 17 preferably contains a solid peroxygen compound such as potassium monopersulfate and a monopersulfate potassium salt reagent, preferably guaiacolsulfonate. This combination of materials is activated by the water in the toilet bowl and is very sensitive to the presence of blood in the solution. It has been found that guaiacolsulfonate and potassium monopersulfate are highly specific and do not under most circumstances yield false positive indications when no blood is present in the solution.

The test pad 12 floats on the surface of the toilet bowl, due to the lightweight paper and selected adhesives of the test pad, to facilitate analysis of the test. The test pad 12 is preferably biodegradable to permit disposing of the test pad 12 by simply flushing the toilet after the test is completed.

It is preferred that the top layer 15 of the test pad include blue-green pigmentation to provide a good contrast with the red-orange colored compound formed when the guaicolsulfonate and potassium monopersulfate are catalyzed by blood.

The top and bottom layers 15 and 16 of the test pad 12 are preferably bonded together by means of an adhesive or a heat seal process which is effective to keep the reagent materials in place on the test pad 12.

A positive control 18 may also be included on the test pad 12 to indicate when the result of the test is falsely negative. The positive control 18 includes the solid peroxygen compound and the reagent as well as a small amount of a catalyzing agent such as hemoglobin which will in all cases cause the positive control 18 to undergo the chromogen reaction yielding a red-orange colored compound if the reagent and peroxygen compound are present and functioning properly. The quantity of catalyst in the positive control 18 should be limited so that all of the catalyst is used up by the reagent in the control 18 and is not permitted to migrate to the test area 17. If the positive control 18 fails to undergo the chromogen reaction the test results should be disregarded since all of the components for a positive test result are present in the positive control.

The positive control 18 also provides an example for comparison with the test area if the test area undergoes a chromogen reaction.

A negative control 18 may also be provided that should not undergo a chromogen reaction. The negative control 19 would contain a substance having a similar appearance to the substance contained in the test area 17. The substance in the negative control 19 may be the solid peroxygen compound without any of the solid reagent material. The peroxygen compound should not undergo a chromogen reaction unless the test pad is contaminated, manufactured improperly, or an interfering substance is present in the toilet bowl.

The negative control 19 may also be used as a point of reference for the test area 17 when no chromogen reaction occurs at the test area 17. If the negative control 19 and the test area 17 have the same appearance after the test has been performed the patient may then assume that the test was negative.

Figures 2, 3:
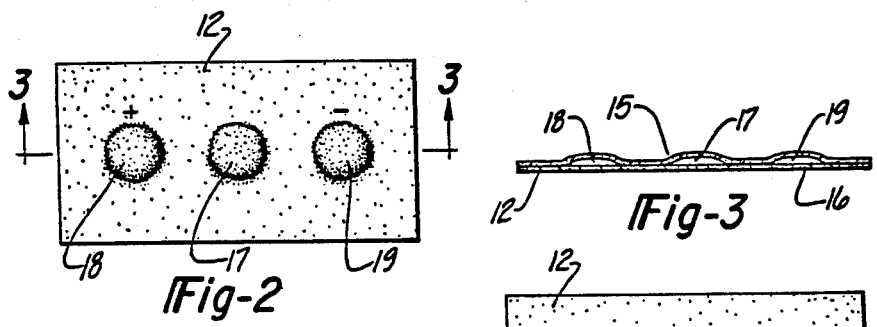
FIG. 2 is a plan view of the test pad having a test area, a comparative positive site and a comparative negative site.
FIG. 3 is a cross-sectional view taken along the line 3—3 in FIG. 2.
Figures 4, 5:
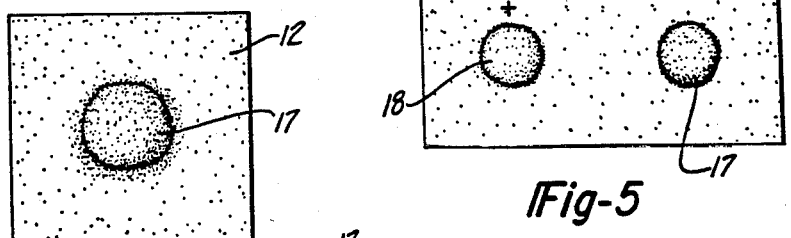
FIG. 4 is a test pad having a single deposit of reagent material in a test area.
FIG. 5 is a test pad having a test area and a comparative positive site.
Figure 6:
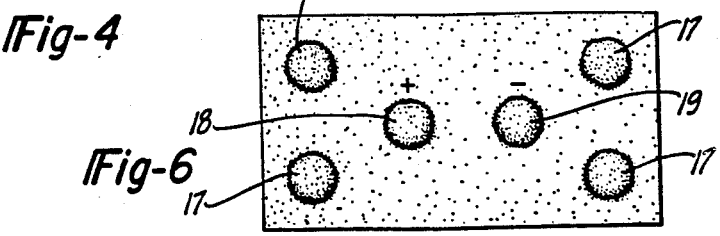
FIG. 6 is a test pad having a plurality of spaced apart test areas, a comparative positive site and a comparative negative site.

As shown in FIGS. 1, 2 and 3, the test pad may include positive and negative controls 18 and 19 in addition to the test area 17. Alternatively, as shown in FIG. 4, the test pad may include only the test area 17. Or, as shown in FIG. 5, the test pad may include the test area 17 and positive control 18. In another alternative, shown in FIG. 6, more than one test area 17 may be provided on a pad 12 to permit verification of a test with a single pad 12. Positive and negative controls 18 and 19 are also provided for comparison purposes as previously described.

An example of a reagent and solid peroxygen compound combination may be equal parts of potassium guaiacolsulfonate (PGS), a guaiac substitute material also known as 1-hydroxy-2-methoxy-benzene-4 (or -5) sulfonic acid, and a compound (MPS) sold by DuPont Co. under the trademark "Oxone" which comprises two moles of potassium monopersulfate, one mole of potassium hydrogen sulfate and one mole of potassium sulfate. Depending upon the purity or strength of the PGS, the acceptable range of mixtures may vary from $\frac{1}{3}$ PGS and $\frac{2}{3}$ Oxone to $\frac{2}{3}$ PGS and $\frac{1}{3}$ Oxone. Both the peroxygen compound and reagent are known industrial chemical products.

When used together in a test pad the preferred peroxygen compound and reagent offer sensitivity and specificity not realized in the prior art products. PGS has the chemical formula $C_7H_7KO_5S$ or in its dipotassium water complex form $C_7H_7K_2O_5S \cdot H_2O$ with the chemical structure as follows:

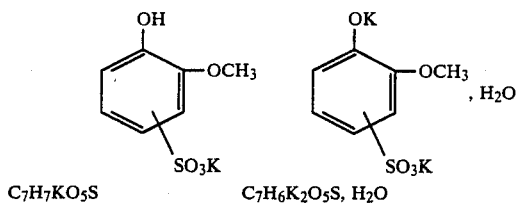

C₇H₇KO₅S      C₇H₆K₂O₅S, H₂O

One important advantage of PGS is that it is freely soluble in water within a wide range of temperatures. Another advantage is that PGS is not a suspected carcinogenic chemical. PGS is a chromogen which yields a red-orange color when exposed to an appropriate oxidizing substance. PGS is safe to use and eliminates the need for a patient to use caustic solutions of alcoholic peroxide as recommended by some prior art tests.

The preferred compound, identified hereinafter as MPS, has the chemical formula $2KHSO_5 \cdot KHSO_4 \cdot K_2SO_4$, with the major component having the chemical structure:

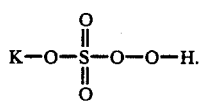

Oxone is soluble in water and actively releases oxygen. Oxone is a triple salt which has been found to yield superior results than a combination of its three component salts. Oxone is not as sensitive to trace metal impurities as most peroxygen compounds, while cobalt, nickel, copper, and manganese ions will catalyze the decomposition of Oxone with the evolution of oxygen gas, this catalysis does not interfere with the occult blood test in levels normally encountered in a toilet bowl.

Specificity

The mixture of PGS and MPS powder in a test pad also exhibits superior specificity in testing for blood in a solution. The mixture proposed by the present invention is less likely to result in false positive tests because it is not effected by metal ions and other contaminants commonly found in a toilet bowl.

The following chart represents an analysis of the present invention, denoted MPS/PGS, as compared to guaiac impregnated paper activated by an alcoholic hydrogen peroxide solution. The guaiac impregnated paper and alcoholic hydrogen peroxide system used is currently sold by Helena Laboratories under the trademark ColoScreen. In the test the MPS/PGS system and ColoScreen kit were exposed to various solutions including the substances listed in the left column. The results of the test are set forth in Table I.

TABLE I

| Specimen | ColoScreen | MPS/PGS |
| --- | --- | --- |
| Water | − | − |
| Horseradish Peroxidase | + + + + | + |
| Fe⁺³ ion | + + | − |
| Fe⁺² ion | + + | − |
| Urine | − | − |
| CuCl₂ | + + + + + | − |
| CaCl₂ | + + | − |
| Cu(OH)₂ (Not in solution) | − | − |
| Cu(C₂H₃O₂)₂ | + + + + + | − |
| Pb(C₂H₃O₂)₂ | + + + | − |
| NaHOCl (5.25%) | + + + + | + |
| Cleanser | − | + |
| Na₂CO₃ | − | − |

Legend:
− No Color Change
+ Color Change
++ Pronounced Color Change
+++ Strong Color Change
++++ Very Strong Color Change
+++++ Maximum Color Change

Sensitivity

The mixture of PGS and MPS powder in the test pad exhibits excellent sensitivity to the presence of occult blood in very small quantities. The sensitivity has been determined to be relatively unaffected by contaminants commonly found in a toilet bowl.

The sensitivity to hemoglobin of the MPS/PGS system was tested in solutions having different concentrates of $FeSO_4$. The purpose of the test being to determine the effect of $FeSO_4$ on the chromogen reaction catalyzed by hemoglobin. The results of the test are set forth in Table II.

TABLE II

| Hemoglobin Concentration | Water | 1 mg % | 2 mg % Hemo. | 4 mg % Hemo. |
| --- | --- | --- | --- | --- |
| FeSO₄ Concentration | | | | |
| 600 mg % (1.5 × 10⁻³ mole %) | ± | +_+ | + | + |
| 400 mg % (1.0 × 10⁻³ mole %) | _+_ | ± | + | + |
| 200 mg % (5.1 × 10⁻⁴ mole %) | − | ± | + | + |
| 100 mg % (2.5 × 10⁻⁴ mole %) | − | _+_ | ± | + |
| 0 mg % | − | _+_ | ± | + |

Legend:
_+_ Minor Trace
± Trace
+_+ Minor Color Change
+ Color Change

Thus, the test indicates sensitivity is not adversely affected by iron compounds in the solution. In extreme concentrations of 400 mg % to 600 mg %, where an iron precipitate is observable a color change may occur in the water surrounding the pad but not at the site of the reaction. Such a reaction occurs after two minutes and would not be confused with a positive test. However, the test is sensitive to very small concentrations of hemoglobin (1 mg%) regardless of the amount of iron in the sample.

This feature is important because iron is frequently present in toilet bowl water of older buildings or it may be present in the feces or urine of a patient. It has been determined that the MPS/PGS system does not undergo a color change until approximately $1 \times 10^{-2}$ M. of $Fe^{+2}$ ion or $4 \times 10^{-2}$ M. of $Fe^{+3}$ ion is present in the solution.

When MPS and potassium guiacolsulfonate (PGS) are combined in the test pad of the present invention, the sensitivity of the chemicals to blood in a solution is equivalent to that of the combination proposed by Friend in his U.S. Pat. No. 4,175,923 which requires the use of a strong caustic alcohol peroxide solution.

The sensitivity of the MPS/PGS system was evaluated in solutions containing an iron sulfate and varying amounts of hemoglobin with the result that sensitivity was found to be unaffected.

The invention has been in described in conjunction with a specific embodiment, however, there are many alternatives, modifications and variations will be apparent to those skilled in the art in light of the foregoing description. Accordingly, the invention is intended to embrace all such alternatives, modifications and variations that fall within the scope of the appended claims.

I now claim:

1. A test composition in solid form for the detection of blood in an aqueous solution which comprises a water soluble oxidizing agent and a water soluble guaiacolsulfonate whereby when blood in an aqueous solution is added to said test composition, such blood causes catalytic reduction of the oxidizing agent with subsequent generation of an oxidized donor to cause a chromogen reaction with the guaiacolsulfonate, said oxidizing agent having the chemical formula $2KHSO_5 \cdot KHSO_4 \cdot K_2SO_4$.

2. The test composition of claim 1 wherein the oxidizing agent and the guaiacolsulfonate are intermixed on a substrate.

3. The test composition of claim 1 wherein the oxidizing agent and the guaiacolsulfonate are a powder mixture.

* * * * *